United States Patent [19]

Fisher et al.

[11] Patent Number: 4,596,137
[45] Date of Patent: Jun. 24, 1986

[54] METHOD AND APPARATUS FOR MEASURING THE PENETRATION OF FLUIDS

[75] Inventors: C. Donald Fisher, Glencoe; John A. Cutcher, Westchester, both of Ill.

[73] Assignee: Viscosity Oil Co., Chicago, Ill.

[21] Appl. No.: 710,051

[22] Filed: Mar. 11, 1985

[51] Int. Cl.$^4$ ............... G01N 13/02; G01N 33/30
[52] U.S. Cl. .................................... 73/64; 73/54; 73/64.4
[58] Field of Search ............... 73/64, 54, 61.1 C, 55, 73/64.4

[56] References Cited

U.S. PATENT DOCUMENTS 3,358,496  12/1967  Farmer .................... 73/61.1 C

FOREIGN PATENT DOCUMENTS 401022  8/1924  Fed. Rep. of Germany .......... 73/64

Primary Examiner—Stewart J. Levy
Assistant Examiner—Joseph W. Roskos
Attorney, Agent, or Firm—McDougall, Hersh & Scott

[57] ABSTRACT

A method and apparatus for measuring the penetration of fluids which includes a sandwich formed of a substantially flat plate means adapted to have a portion thereof immersed in a fluid and a cover plate in surface contact therewith and clamp means to secure the cover plate in surface contact with the flat plate. When the sandwich is immersed in a fluid to be measured, the fluid is drawn upwardly in the interstices between the flat plate and the cover plate at a rate which is a measure of the penetration of the fluid.

6 Claims, 2 Drawing Figures

METHOD AND APPARATUS FOR MEASURING THE PENETRATION OF FLUIDS

This invention relates to a method and apparatus for measuring the penetration of fluids, and more particularly to a method and apparatus for accurately measuring the penetration of liquids such as liquid lubricants.

As is well known to those skilled in the art, quite a number of different techniques have evolved over the years to measure the viscosity of liquids, and particularly the viscosity of lubricating liquids. Thus, viscosity is used to define some properties of lubricating liquids. Surface tension is also widely used as an indication of the wetting properties of liquids, including liquid lubricants. Despite the fact that those two characteristics define physical properties of lubricants, there is still no readily available means to measure the penetration of a lubricant, that is, the tendency of a lubricant to penetrate interstices between two parts which are secured together.

It is accordingly an object of the present invention to provide a technique for simply and efficiently measuring the penetration properties of a fluid.

It is a more specific object of the present invention to provide a method and apparatus to measure quantitatively the penetration of fluids, and particularly the penetration of lubricating liquids.

These and other objects and advantages of the invention will be described more fully hereinafter, and, for purposes of illustration but not of limitation, an embodiment of the invention is shown in the accompanying drawings wherein.

The concepts of the present invention reside in a method and apparatus for measuring the penetration of fluids which utilize a substantially flat plate which is adapted to have its lower portion immersed in a fluid for which the penetration is to be measured. In face contact with that plate is a cover plate, which is preferably a transparent plate such as glass, and is adapted to be placed in surface contact with the flat plate to cover at least a part of the lower surface of the flat plate. The cover plate is urged toward surface contact with the flat plate by means of suitable clamp means. Because of the forces of surface tension and other undetermined properties of the fluid, when the assembly of the flat plate and the cover plate in surface contact is immersed in the fluid, the fluid is drawn into the fluid-penetrable interstices between the flat plate and the cover plate at a rate which is a measure of the penetration of the liquid. The technique of the present invention thus provides an extremely simple and efficient means of measuring the ability of a liquid, such as a lubricating liquid, to penetrate the interstices between two parts which are secured together.

Figure 1:
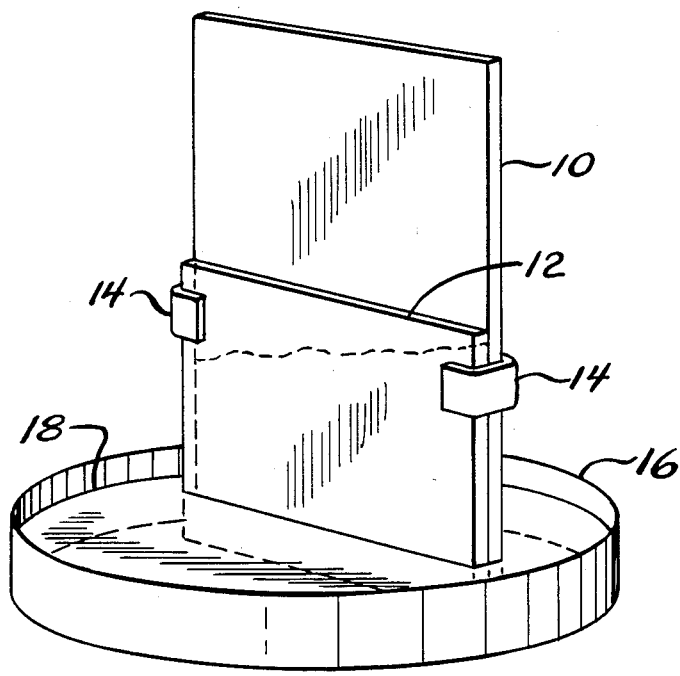
FIG. 1 is a perspective view showing the apparatus employed in the practice of this invention.
Figure 2:
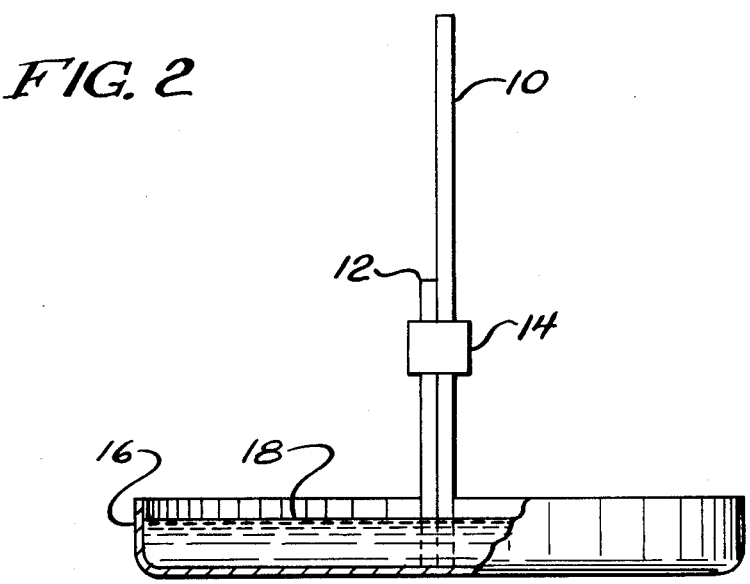
FIG. 2 is a side view of the apparatus illustrated in FIG. 1.

Referring now to the drawings for a more detailed description of the invention, there is shown in FIGS. 1 and 2 a substantially flat plate 10 which is preferably formed of a metal, such as stainless steel, having a smooth surface. A cover plate 12 is provided, preferably a flat plate which is transparent or at least translucent and is adapted to be placed in surface contact with the lower portion of the flat plate 10 to define small fluid-penetrable interstices between the flat plate 10 and the cover plate 12. To secure the cover plate in surface contact with the flat plate 10, there is preferably provided one or more clamp means 14, schematically illustrated in FIGS. 1 and 2, which serve to urge the cover plate 12 toward surface contact with the flat plate 10, leaving only small interstices therebetween. The clamp means 14 can be any of a variety of clamps well known to those skilled in the art, and are preferably spring clamp means which serve to urge the cover plate 12 toward surface contact with the flat plate 10.

When the sandwich of the cover plate 12 and the flat plate 10 in surface contact therebetween are immersed in a vessel 16 containing a level 18 of, for example, a liquid lubricant, physical and chemical forces of the fluid serve to cause the liquid level to migrate upwardly from the surface of the liquid 18 in the interstices between the flat plate 10 and the cover plate 12. The rate of movement of the liquid through those interstices is a measure of the penetration of a liquid in the vessel 16 (which may conveniently be a Petri dish).

It has been found that the rate of migration of the liquid through the interstices between the cover plate 12 and the flat plate 10 can be reliably used to determine the penetration of a variety of liquid lubricants, regardless of the surface tension of the lubricant. For example, the rate at which the liquid is elevated in the interstices between the cover plate 12 and the flat plate 10 from the liquid level to the top of the cover plate 12 can thus be timed as a means of comparing the penetration of two or more liquid lubricants. To that end, it is possible, and sometimes desirable, to provide the cover plate 12 with graduations marked thereon so that relative rates of travel of the liquid in the interstices between the cover plate 12 and the flat plate 10 can be determined.

The concepts of the present invention have been used to measure the penetration, measured in time, of a variety of lubricants. The results of those tests are set forth in the following table:

| Product | % Non-Volatile | Specific Gravity | Surface Tension (dynes/cm) | Penetration (min:sec) |
| --- | --- | --- | --- | --- |
| VOC4584 | 30 | 0.81 | 24.1 | 2:10 |
| Dupont Wet | 33 | 0.80 | 23.8 | 1:27, 1:37 |
| Breakfree | 65 | 0.96 | 25.8 | 20:00 |
| CRC336 | 23 | 0.92 | 25.4 | 4:55 |
| CRC556 | 19 | 0.82 | 24.9 | 6:00 |
| LPS1 | 4 | 0.80 | 24.1 | 3:40 |
| 3 in 1 | 73 | 0.85 | 26.2 | 20:00 |
| Liquid Wrench | 0.1 | 0.81 | 25.4 | 2:17 |
| Water | 0.0 | 1.00 | 61.0 | 1:55 |
| Kerosene | 0.0 | 0.81 | 25.4 | 1:25 |
| WD40 | 25 | 0.82 | 25.0 | 3:07 |
| Triflow | 58 | 0.92 | 23.2 | 20:00 |
| Starett M1 | 12 | 0.80 | 24.5 | 2:50 |

It will be understood that various changes and modifications can be made in the details of procedures and use without departing from the spirit of the invention, especially as defined in the following claims.

We claim:

1. Apparatus for measuring the penetration of fluids comprising:
   (a) a substantially flat plate means adapted to have a lower portion thereof immersed in a fluid;
   (b) cover plate means adapted to be placed in surface contact with the flat plate means to cover a part of the surface thereof including said lower portion, and (c) means to urge the cover plate means toward surface contact with the flat plate means
whereby fluid is drawn between the flat plate means and the cover plate means at a rate which is a measure of the penetration of the fluid.

2. Apparatus as defined in claim 1 wherein the cover plate means is a transparent plate.

3. Apparatus as defined in claim 1 wherein the means to urge the cover plate is a spring clamp.

4. A method for measuring the penetration of fluids comprising the steps of immersing a portion of a sandwich formed of a substantially flat plate in surface contact with a cover plate into a fluid to be measured and determining the rate at which the fluid is drawn between the flat plate and the cover plate as a measure of the penetration of the fluid.

5. A method as defined in claim 4 wherein the flat plate is a metal plate.

6. A method as defined in claim 4 wherein the cover plate is substantially transparent.

* * * * *